United States Patent
Lam et al.

(10) Patent No.: US 6,745,136 B2
(45) Date of Patent: Jun. 1, 2004

(54) PIPE INSPECTION SYSTEMS AND METHODS

(75) Inventors: Clive Chemo Lam, Tomball, TX (US); John Edward Harris, Friendswood, TX (US)

(73) Assignee: Varco I/P, Inc., Houston, TX (US)

( * ) Notice: Subject to any disclaimer, the term of this patent is extended or adjusted under 35 U.S.C. 154(b) by 0 days.

(21) Appl. No.: 10/189,059

(22) Filed: Jul. 2, 2002

(65) Prior Publication Data

US 2004/0006437 A1 Jan. 8, 2004

(51) Int. Cl.[7] .......................... G01F 17/00; G01F 23/00; G01F 19/00; G01L 7/00; G01N 11/00
(52) U.S. Cl. .................. 702/54; 73/622; 73/865.8; 73/629; 73/623; 73/601; 356/631; 356/635; 378/58; 324/204; 324/220; 324/226
(58) Field of Search .................. 702/54; 73/865.8, 73/629; 356/631, 635; 378/58; 324/204, 220

(56) References Cited

U.S. PATENT DOCUMENTS

| | | | |
|---|---|---|---|
| 3,437,917 A | 4/1969 | Gunkel et al. | |
| 3,455,150 A | 7/1969 | Wood | |
| 3,489,679 A | 1/1970 | Davidson et al. | |
| 3,741,003 A | 6/1973 | Gunkel | 73/67.7 |
| 3,759,090 A | 9/1973 | McFaul et al. | 73/67.6 |
| 3,766,775 A | 10/1973 | Gunkel | 73/67.8 S |
| 3,868,847 A | 3/1975 | Gunkel | 73/67.8 S |
| 3,916,699 A | * 11/1975 | Moran et al. | 73/623 |
| 3,918,294 A | 11/1975 | Makino et al. | 73/67.2 |
| 3,942,358 A | 3/1976 | Pies | 73/67.7 |
| 3,949,227 A | 4/1976 | Gambini et al. | 250/358 P |
| 3,969,926 A | 7/1976 | Walker et al. | 73/67.8 S |
| 3,974,684 A | 8/1976 | Roule et al. | 73/71.5 US |
| 3,975,948 A | 8/1976 | Makino et al. | 73/67.2 |
| 3,981,184 A | 9/1976 | Matay | 73/67.8 S |
| 3,985,022 A | 10/1976 | Dileo | 73/67.8 R |
| 3,986,389 A | 10/1976 | Mesina et al. | 73/67.9 |
| 3,991,607 A | 11/1976 | Niklas | 73/67.7 |
| 3,992,925 A | 11/1976 | Perilhou | 73/67.7 |
| 3,994,154 A | 11/1976 | Niklas et al. | 73/67.8 R |
| 3,996,792 A | 12/1976 | Kubota et al. | 73/67.8 S |
| 3,999,422 A | 12/1976 | Lehmann et al. | 73/67.8 S |
| 4,003,244 A | 1/1977 | O'Brien et al. | 73/67.8 R |
| 4,004,454 A | 1/1977 | Matay | 73/67.8 R |
| 4,010,635 A | 3/1977 | Patsey | 73/67.85 |
| 4,011,750 A | 3/1977 | Robinson | 73/67.7 |
| 4,012,946 A | 3/1977 | Patsey | 73/67.7 |
| 4,026,144 A | 5/1977 | Gericke et al. | 73/67.6 |

(List continued on next page.)

FOREIGN PATENT DOCUMENTS

| | | |
|---|---|---|
| GB | 2124379 A | 7/1983 |
| GB | 2280507 A | 7/1993 |
| SU | 480-973 | 8/1975 |

OTHER PUBLICATIONS

Ultrasonic NDT Instruments and Systems, Matec Instrument Companies 2001.
CFER., Center for Frontier Engineering Research, Annual Report 1986–87, p. 9, p. 8.
Abstract For Russia SU 480–975.

*Primary Examiner*—John Barlow
*Assistant Examiner*—Aditya Bhat
(74) *Attorney, Agent, or Firm*—Guy McClung

(57) ABSTRACT

A method for inspecting pipe, the method, in at least certain aspects, including detecting an inspection parameter in at least a first part of a pipe, the pipe having a length, a hollow body, an outer surface, and a generally circular pipe wall with an inner diameter and an outer diameter, locating at a first location the first part of the pipe with respect to the length of the pipe and with respect to the outer diameter of the pipe; and such a method for inspecting pipe which, in at least certain aspects, includes detecting at least a first part of a first imperfection of the pipe.

35 Claims, 3 Drawing Sheets

U.S. PATENT DOCUMENTS

| | | | |
|---|---|---|---|
| 4,062,227 A | 12/1977 | Heyman | 73/630 |
| 4,078,427 A | 3/1978 | Yoshida et al. | 73/194 A |
| 4,404,853 A | 9/1983 | Livingston | 73/522 |
| 4,471,657 A | 9/1984 | Voris et al. | 73/597 |
| 4,475,399 A | 10/1984 | Livingston | 73/622 |
| 4,487,072 A | 12/1984 | Livingston | 73/622 |
| 4,541,064 A | 9/1985 | Livingston | 364/552 |
| 4,569,229 A | 2/1986 | de Halleux | 73/597 |
| 4,700,576 A | 10/1987 | Grare et al. | 73/761 |
| 4,718,277 A | 1/1988 | Glascock | 73/622 |
| 4,735,269 A | 4/1988 | Park et al. | 175/46 |
| 4,846,001 A | 7/1989 | Kibblewhite | 73/761 |
| 4,870,866 A | 10/1989 | Slack | 73/599 |
| 5,313,837 A | 5/1994 | Haynes | 73/627 |
| 5,333,502 A * | 8/1994 | Clark et al. | 73/623 |
| 5,392,652 A | 2/1995 | Levesque et al. | 73/629 |
| 5,400,645 A | 3/1995 | Kunze et al. | 73/40.5 A |
| 5,419,334 A | 5/1995 | Miyagawa | 128/662.06 |
| 5,460,046 A | 10/1995 | Maltby et al. | 73/623 |
| 5,534,775 A | 7/1996 | Lam et al. | 324/216 |
| 5,600,069 A | 2/1997 | Girndt et al. | 73/622 |
| 5,656,786 A * | 8/1997 | Curtis et al. | 73/865.8 |
| 5,828,723 A * | 10/1998 | Mariscotti | 378/58 |
| 5,867,275 A * | 2/1999 | Curtis et al. | 356/635 |
| 5,914,596 A | 6/1999 | Weinbaum | 324/228 |
| 6,091,500 A * | 7/2000 | Bahr et al. | 356/631 |
| 6,230,568 B1 | 5/2001 | Winston et al. | 73/601 |
| 6,230,799 B1 | 5/2001 | Slaughter et al. | 166/249 |
| 6,231,510 B1 | 5/2001 | Negrin et al. | 600/443 |
| 6,231,511 B1 | 5/2001 | Bae | 600/447 |
| 6,231,513 B1 | 5/2001 | Daum et al. | 600/458 |
| 6,249,119 B1 | 6/2001 | Curtis, Jr. et al. | 324/242 |
| 6,398,731 B1 | 6/2002 | Mumm et al. | 600/437 |

* cited by examiner

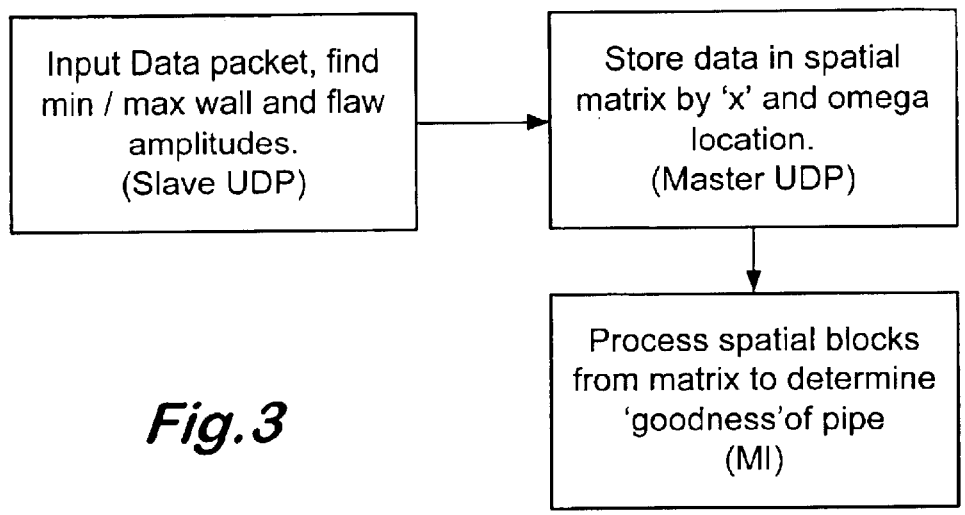

Fig.3

| | | x | x+1 | | | x+k |
|---|---|---|---|---|---|---|
| | n | UT Data | UT Data | UT Data | UT Data | UT Data |
| | n+1 | UT Data | UT Data | UT Data | UT Data | UT Data |
| | | UT Data | UT Data | UT Data | UT Data | UT Data |
| | | UT Data | UT Data | UT Data | UT Data | UT Data |
| | | UT Data | UT Data | UT Data | UT Data | UT Data |
| | | UT Data | UT Data | UT Data | UT Data | UT Data |
| | | UT Data | UT Data | UT Data | UT Data | UT Data |
| Radial Location | | UT Data | UT Data | UT Data | UT Data | UT Data |
| | | UT Data | UT Data | UT Data | UT Data | UT Data |
| | | UT Data | UT Data | UT Data | UT Data | UT Data |
| | | UT Data | UT Data | UT Data | UT Data | UT Data |
| | | UT Data | UT Data | UT Data | UT Data | UT Data |
| | | UT Data | UT Data | UT Data | UT Data | UT Data |
| | | UT Data | UT Data | UT Data | UT Data | UT Data |
| | n+m | UT Data | UT Data | UT Data | UT Data | UT Data |
| | | x | x+1 | | | x+k |
| | | | | "X" Location | | |

Fig.4 *Data Matrix*

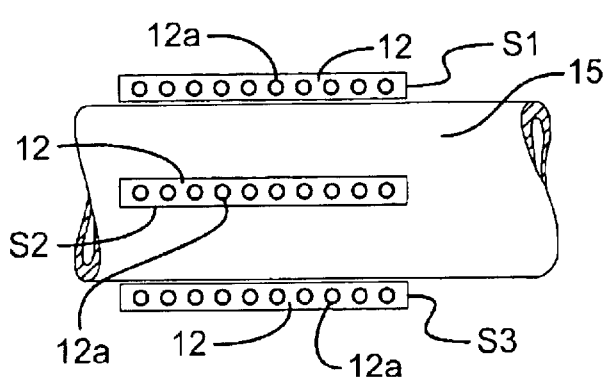
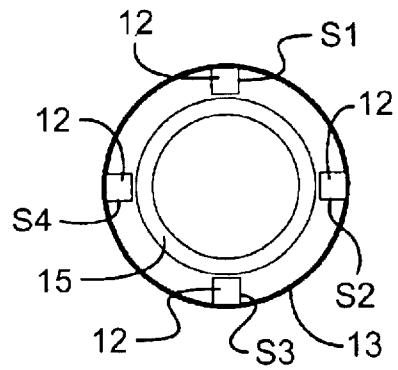
Fig.5A  Fig.5B
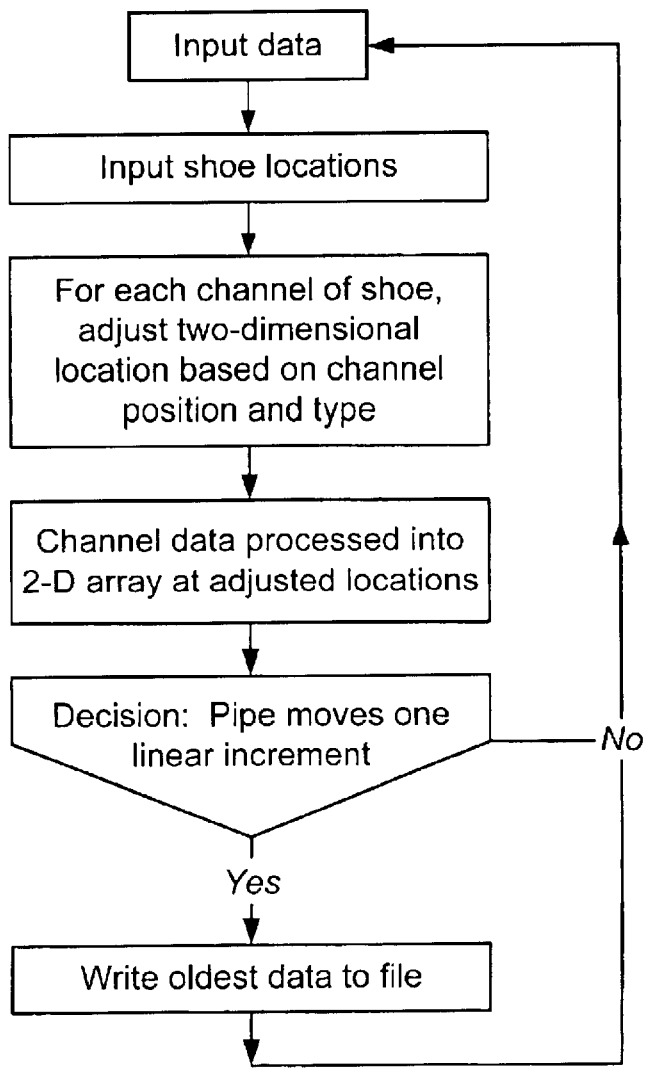
Fig.6

PIPE INSPECTION SYSTEMS AND METHODS

BACKGROUND OF THE INVENTION

1. Field of the Invention

The present invention is directed to pipe inspection systems and methods; such systems and methods using ultrasonic inspection apparatus; such systems and methods which provide a presentation of inspection parameter data correlated with a precise two-dimensional location on the pipe; and, in at least certain aspects, methods for categorizing a plurality of acceptable pieces of pipe according to relative strength and/or risk criteria.

2. Description of Related Art

In one known prior art ultrasonic pipe inspection system, generated inspection data corresponding to a measurement of the wall thickness of a pipe was presented in terms of a longitudinal one-dimensional location on the pipe. Such data is presented graphically as an x-y graph with signal amplitude (corresponding to pipe wall thickness) on the y-axis and longitudinal location on the pipe on the x-axis, but with no indication regarding where on the 360 degree circumference at that longitudinal location the wall thickness was measured. Such prior art systems do not provide a precise correlation between a particular wall thickness indication (which may be an average of multiple measurements) and an exact (in two dimensions) location on the pipe. Such prior art systems often provide only an average pipe wall thickness over a pre-selected length of the pipe and thus do not and cannot distinguish between randomly scattered discrete, separate areas of below-average wall thickness and relatively continuous areas that extend continuously along a portion of the pipe's length. Such scattered discrete areas may have a less deleterious effect on overall pipe strength than a single continuous area. Thus an entity with a plurality of pieces of pipe, all judged "acceptable" according to some preselected strength criteria, cannot select (using data obtainable by prior art systems), "stronger" or less risky pipe for use in more stressful locations and "weaker" or more risky pipe for use in less stressful locations. For example, when the pipe is used in a drill string in a wellbore drilling operation, it is desirable to have the strongest or least risky pipe at the bottom of the string near or adjacent a drill bit since pipe at this location typically undergoes the greatest stress imposed on the drill string.

There is a need, recognized by the present inventors, for an efficient and effective pipe inspection systems which make possible the categorization according to strength and/or failure probabilities of a plurality of acceptable pieces of pipe.

There is a need, recognized by the present inventors, for such systems that provide an accurate correlation between measured pipe wall thickness data and precise two-dimensional location on the pipe.

SUMMARY OF THE PRESENT INVENTION

The present invention, is at least certain aspects, discloses a method for inspecting tubulars, e.g., pipe, casing, tubing and risers ("pipe"), the method including detecting an inspection parameter in at least a first part of a pipe, the pipe having a length, a hollow body, an outer surface, and a generally circular pipe wall with an inner diameter and an outer diameter, and then locating at a first location the first part of the pipe with respect to two dimensions of the pipe, e.g., with respect to the the length of the pipe and with respect to the outer diameter of the pipe.

The present invention, in at least certain aspects, discloses a method for inspecting pipe that includes detecting at least a first part of a first imperfection in a parameter (e.g., but not limited to, wall thickness) of a pipe, the pipe having a length, a hollow body, an outer surface, and a generally circular pipe wall with an inner diameter and an outer diameter, and then locating at a first location the first imperfection with respect to two dimensions of the pipe, e.g., with respect to the length of the pipe and with respect to the outer diameter of the pipe.

The present invention, in at least certain aspects, provides systems and methods for measuring pipe wall thickness along a length of pipe; identifying a location for each wall measurement in terms of two locations or dimensions of the pipe, e.g. a length dimension and a circumferential dimension; and correlating each such location with each such wall thickness measurement. Thus a data listing, table, graph, "map," or grid of the pipe can be generated, according to the present invention, with wall thickness measurements related to relatively precise pipe locations. Such a map, etc. can also indicate continuities from one precise location to another and another, etc., along the pipe length, of equal or near equal wall thickness measurements that can show a continuous area of similar, and in many cases, relatively thin, wall thickness. Also, such a map or grid, etc. can indicate that areas of a particular wall thickness are discrete, random, and/or scattered which may have a relatively smaller impact on overall pipe strength as compared to a continuous length or area of relatively thin wall thickness.

Systems according to the present invention may be used to provide the factual basis to reject a piece of pipe for a particular use; to categorize a number of "acceptable" pieces of pipe according to relative strength so that those pieces that are relatively stronger may be used in locations of greatest stress and/or to provide measurements and pipe location data that is presentable in any desired form or format, including, but not limited to, in a table, in a data matrix, on a graph, in a data listing, or in a combination of these, and such a presentation that is on paper, on a screen or monitor, and/or on a strip chart.

It is, therefore, an object of at least certain preferred embodiments of the present invention to provide:

New, useful, unique, efficient, non-obvious systems and methods for correlating pipe wall thickness measurements with precise locations on the pipe; and Such systems and methods which provide data for categorizing a plurality of pieces of pipe according to relative strength; and Such systems and methods which provide a presentation of such correlations and/or categorization.

The present invention recognizes and addresses the previously-mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or equivalent embodiments.

FIG. 3 shows schematically data flow between parts of the system of FIG. 1.

FIG. 4 shows one graphical presentation of data from the system of FIG. 1.

FIG. 5A is a side schematic view of part of the system of FIG. 1.

FIG. 5B is an end view of the system of FIG. 5A.

FIG. 6 is a flow chart for a program for the system of FIGS. 1 and 2.

DESCRIPTION OF EMBODIMENTS PREFERRED AT THE TIME OF FILING FOR THIS PATENT

Figure 1:
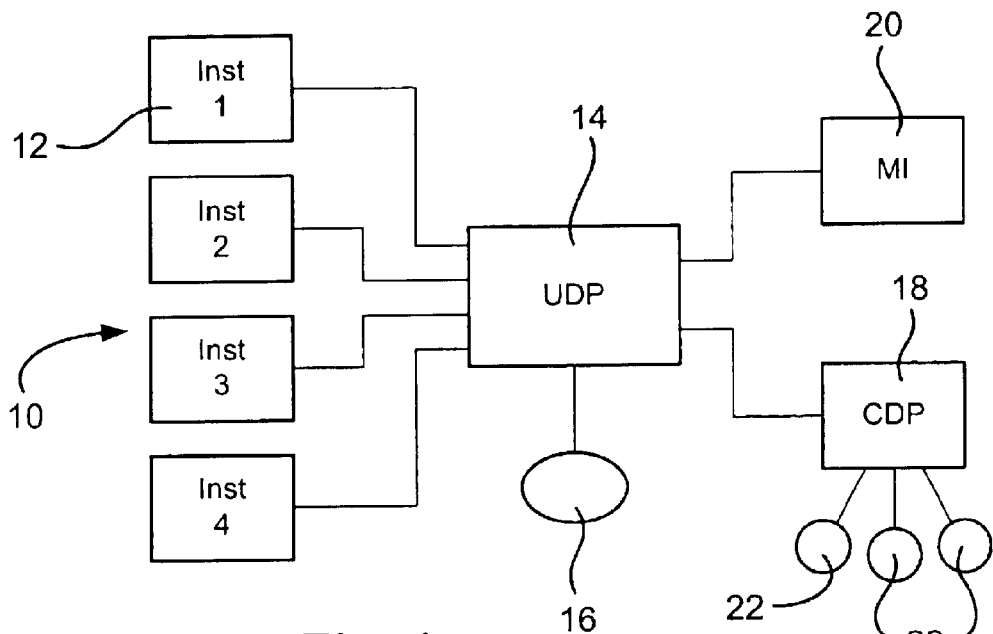
FIG. 1 shows schematically a system according to the present invention.

In one system 10 according to the present invention as shown in FIG. 1, raw data generated by measuring systems with ultrasonic transducers and related instruments 12 ("Inst 1, 2, 3, 4") is sent to one or more ultrasonic data processors 14 ("UDP"). The ultrasonic data processor(s) 14 produce a correlation of wall thickness and, optionally, provide output signals to a graphical display unit 16 (e.g. monitor or screen) and/or to a user-machine interface system 20 ("MI"). Data from the ultrasonic data processor(s) 14 may, optionally, also be sent to a command and data processor 18 ("CDP") which coordinates data from multiple inspection machines 22 (which may, for example, produce measurements of other parameters, e.g., but not limited to, ovality, flux leakage, and grade verification.

Data may be sent from the ultrasonic transducer instruments 12 via Ethernet cable and associated devices, by other suitable means, and/or wirelessly. The output of the ultrasonic data processor(s) 14 is in the form of digital signals and/or display on screen and is sent to the user-machine interface 20 via Ethernet cable, by other suitable means, and/or wirelessly. Output data in the form of digital signals and/or display on screen is also, optionally, sent to the command and data processor 18 by similar apparatus and methods.

The ultrasonic data processor is, in one aspect a computer which is programmed to organize data from the ultrasonic transducer instruments as a two-dimensional graph of the surface of a pipe being inspected (a pipe image) and as a x-versus-signal amplitude graph which presents a specific location on the pipe surface.

In one particular embodiment the pipe surface is divided into a matrix of discrete segments, e.g. 30 segments, each covering 12° of the pipe's 360° circumference; each segment having one dimension that is part of the pipe's total length and another dimension which is part of the pipe's total circumference. For example, with a pipe's length divided into discrete circumferential segments each with a first dimension that is 1" of the pipe's length, the other dimension will be $Y_z$," i.e., when the pipe surface is viewed as a flattened out rectangle, each segment has a longitudinal dimension of 1" and a vertical dimension of ½. The ultrasonic transducer instruments produce a signal indicative of a pipe wall thickness measurement for each discrete 1"×½ segment. An analysis of the pipe can be performed with the 2-dimensional input data from the UDP 14 using 2-dimensional processing in the machine interface 20 or other appropriate apparatus. In certain particular aspects the range of dimensions for the pipe segments is between ⅛" to 2" and in other aspects between 1 cm. and 50 mm.

Figure 2:
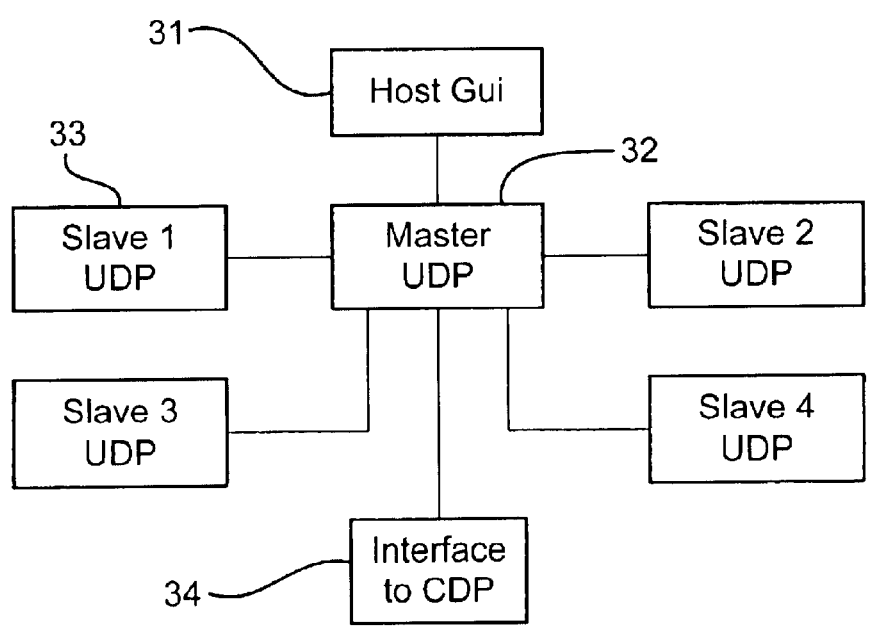
FIG. 2 shows schematically parts of subsystems of the system of FIG. 1.

In one embodiment of a system 10 according to the present invention, the machine interface 20, as shown in FIG. 2 has a graphical user interface 31 ["Host Gui" (MMI)] for adjusting and configuring the instruments 12; and for accessing, directing, and controlling a master subsystem 32 ("Master UDP") which itself controls multiple slave subsystems 33 ("Slave 1, UDP, Slave 2, UDP, etc.).

An interface subsystem 34 ("Interface to CDP") provides an interface between the ultrasonic data processor 14's master subsystem 32 and the command and data processor 18. The master subsystem 32 and the slave subsystems 33 may be any suitable computer or computerized system or apparatus. In one particular aspect of the ultrasonic data processor 14, the graphical user interface 31 is an appropriately programmed computer, e.g., but not limited to a computer with a Windows 2000 operating system; the master subsystem 32 is a similar computer; the slave subsystems 33 are similar computers; and the interface subsystem 34 is a similar computer; but it is within the scope of this invention for all of the functions of all of these to be one appropriately powerful computer.

The master subsystem 32 consolidates the output from the slave subsystems 33; computes per revolution pipe wall thickness measurements (revolution of a head with the ultrasonic transducer systems on it); transmits processed inspection data to the command and data processor 18 to the graphical user interface 31 that is, optionally, presented e.g. on a monitor or screen. e.g. maximum and minimum wall thickness and/or flaw amplitudes as a percent of full scale longitudinal inner diameter flaw amplitude, longitudinal outer diameter flaw amplitude, transverse inner diameter and outer diameter, and multiple categories of oblique flaws (e.g., at three different angles) for both inner and outer diameter; and the master subsystem steers user commands from the graphical user interface 31 to a (or the) slave subsystem(s) and/or ultrasonic transducer instrument(s) 12.

The slave subsystems 33 reduce information band width by deleting all signals that do not reach a certain pre-selected "peak qualified" amplitude (i.e., signals that do not indicate a flaw or anomaly that has been predetermined to be insignificant), and they produce error corrected results, e.g. average wall thickness.

The user-machine interface system 20 directs or "loads" the instruments 12 with configuration information (which may, e.g., include ultrasonic control settings) and loads the ultrasonic data processor 14 with configuration and calibration parameters, e.g. for adjustments to obtain real wall thickness. The user-machine interface system 20 provides a system operator with control of the pipe inspection process and does this on a per-channel basis for each instrument and/or for each transducer. The user-machine interface system 20 can, optionally, display inspection data in real time as an inspection trace on a monitor or screen or on a strip-chart output. The user-machine interface optionally, in certain aspects, provides a pipe image in color or black and white showing flaws in the pipe or wall thickness anomalies. The user-machine interface 20 in certain aspects, prints an image from a screen automatically or upon operator request; saves inspection data to a hard disc; and/or replays inspection data from a selected file or files.

The command and data processor 18, in certain aspects, provides a printed report for a particular joint of pipe that has been inspected; saves the report as a file; and/or produces a chart, grid or map that shows the flaw signal amplitude for each discrete segment of the pipe.

FIG. 3 shows schematically the flow of data from one or more slave subsystem 33 to the master subsystem 32 and to the user-machine interface 20. The slave subsystem(s) 33 receive the input data ("Input data packet") from the instruments 12 and determine minimum and maximum wall thickness signal and flaw signal amplitudes. The master subsystem 32 processes the data from the slave subsystems to produce a two-dimensional (e.g. "'x" and omega" or length along pipe vs. circumferential segment location). The master subsystem 32 then sends its results (e.g. map, table, chart, grid) to the machine interface system 20 which, optionally, processes the map etc. data, analyses it, and/or categorizes and/or determines relative strength for the pipe (determines 'goodness' of pipe).

FIG. 4 is one embodiment of a graphical presentation format or "map" for presenting data according to the present invention with a system according to the present invention. The x-axis is the length of the pipe that is inspected. The y-axis is the radial or circumferential location of a discrete pipe segment. The first increment ($\frac{1}{8}$" to 2", in one aspect one inch) of the inspected pipe is "x"; the next increment is "x+1"; and the last increment is "x+k"; "n" is the first discrete increments radial position; "n+1" is the next; and "n+m" is the last. Of course it is within the scope of the present invention to use any desirable length increment, including, but not limited to, $\frac{1}{8}$", $\frac{1}{4}$", $\frac{3}{8}$", $\frac{1}{2}$", $\frac{5}{8}$", $\frac{3}{4}$", $\frac{7}{8}$", 1", $1\frac{1}{4}$", $1\frac{1}{2}$" and 2"; and the increments may extend radially for any desired amount of the pipe's total circumference, including, but not limited to 3, 5, 6, 10, 12, 20, and 30 degrees.

The "UT Data" for each particular discrete increment of the pipe's surface may include maximum and minimum wall thickness for that increment and/or average wall thickness; and inner and outer flaw signal amplitude for longitudinal, transverse, and oblique (three categories) as percent of full scale.

FIGS. 5A and 5B show schematically one possible instrument location for a pipe inspection system according to the present invention. Ultrasonic transducer instruments 12 on a head 13 move around a pipe 15 that passes through the head 13. The ultrasonic transducer instruments 12 may have any desired number of ultrasonic transducers 12a; and, as shown in FIG. 5A, in this particular embodiment, there are 10 ultrasonic transducers on each of four "shoes" S1, S2, S3, S4.

FIG. 6 presents schematically a diagram of steps in a computer program for programming computers in a system according to the present invention like the systems of FIG. 1 and FIG. 2.

The slave subsystem(s) 33 select the data from the data stream indicating flaws and wall thickness whose signals exceed a predetermined threshold (as described above) and send signals indicative thereof ("input data") to the master subsystem 32. The master subsystem 32 has received data from system apparatuses (encoders, etc.) related to specific locations on the pipe for input data from the slave subsystem (s) 33 ("Input shoe locations"). Optionally, the master subsystem 32 adjusts the data related to specific locations on the pipe based on the actual location of a shoe and its transducers on a per-transducer-channel basis ("For each channel of shoe . . . "). The master subsystem 32 then processes the adjusted channel data and produces the map, etc. which presents the correlation of wall thickness measurements, etc. with precise pipe locations ("channel data processed into 2-D array at adjusted locations"). The master subsystem 32 can discriminate between multiple signals and select the "best" (largest amplitude) signal indicative of a particular measurement or flaw and can use the thus-selected signals in producing the map. If data has been received for all the circumferential segments around the pipe at a particular linear location ("Decision: pipe moves one linear increment") ("Yes:), then the system (which has any suitable known pipe movement apparatus (e.g., as disclosed in, but not limited to, in U.S. applications Ser. No. 09/930,117 filed Aug. 14, 2001; 10/052,237 filed Jan. 18, 2002; and 10/117, 312 filed Apr. 5, 2002- all incorporated fully herein for all purposes) moves the pipe to the next linear increment. If data has not been received for all the circumferential segments at a particular linear location ("No"), the inspection at that location continues with raw data from transducers, input data from the slave subsystems, etc., until all segments around the entire circumference are accounted for. Once all segments around the circumference of a particular linear increment have been completed, the ultrasonic data processor 14's master subsystem 32 sends the data or map for that linear increment to the machine interface 20 and/or to the command and data processor 18. The machine interface 20 receives data from the system 14 and records it. ("Write oldest data to file").

The present invention, therefore, provides in certain, but not necessarily all embodiments, a method for inspecting pipe, the method including detecting an inspection parameter in at least a first part of a pipe, the pipe having a length, a hollow body, an outer surface, and a generally circular pipe wall with an inner diameter and an outer diameter, locating at a first location the first part of the pipe with respect to the length of the pipe and with respect to the outer diameter of the pipe.

Such a method may include one or some of the following, in any possible combination: detecting the inspection parameter for a second part of the pipe in a second location adjacent the first location; detecting the inspection parameter additional parts of the pipe in succeeding adjacent locations adjacent the first location and providing a presentation of data related to the inspection parameter for all inspected parts of the pipe and locations on the pipe of all of said parts; the presentation being a map of the pipe's outer surface divided into a plurality of adjacent locations with data for each location representative of the detected inspection parameter at each location; the inspection parameter of the pipe is wall thickness of the pipe; the inspection parameter of the pipe is representative of a flaw in the pipe; the flaw in the pipe is from the group consisting of longitudinal flaw, transverse flaw and oblique flaw; the inspection parameter is pipe wall thickness detected by ultrasonic inspection apparatus; the pipe length is divided into a continuous series of length increments and the pipe outer diameter is divided into a continuous series of segments for each length increment, and the first location is a particular segment at a particular length increment; the inspection parameter is detected for the entire length of the pipe for the entire body of the pipe providing data for the parameter for the entire pipe; the detecting is done by detecting apparatus and the locating is done by a master computer to which is input location data representative of location of the detecting apparatus with respect to the pipe and to which master computer is input inspection parameter data from the detecting apparatus representative of the inspection parameter; the master computer correlates the location data with the inspection parameter data; the inspection parameter is detected for the entire hollow body of the pipe; the inspection parameter data is provided to the master computer by at least one associated slave computer, the at least one associated slave computer in communication with the detecting apparatus for receiving raw data related to the first location from the detecting apparatus, the at least one associated slave computer processing the raw data to provide the location data for the master computer; the master computer is in communication with a machine interface system, the machine interface system for controlling the master computer; the master computer is in communication with a command and data processor computer and data processor for coordinating data from the master computer with other types of inspection data; the detecting is done by detecting apparatus that includes a plurality of spaced apart shoes, each with a plurality of spaced-apart ultrasonic transducers, the shoes rotatable around the pipe, the detecting apparatus including related ultrasonic transducer instrumentation for providing raw data representative of a detected inspection parameter; the at least one associated slave computer selects best signals representative of the inspection parameter for providing location data to the master computer; the master computer adjusts location data to take into account an actual position of the detecting apparatus; the pipe length is divided into a continuous series of length increments and the pipe outer diameter is divided into a continuous series of segments for each length increment, and the first location is a particular segment at a particular length increment, and wherein the master computer instructs the detecting apparatus to move from a first series of segments for a first linear increment that includes the first location to a next series of segments for a next linear increment only upon completion of detecting of the inspection parameter for all segments of the first series of segments; detecting the inspection parameter for all series of segments for all linear increments; and/or each segment having data representative of the inspection parameter for that segment.

The present invention, therefore, provides in certain, but not necessarily all embodiments, a method for inspecting pipe, the method including detecting at least a first part of a first imperfection in a parameter of a pipe, the pipe having a length, a hollow body, an outer surface, and a generally circular pipe wall with an inner diameter and an outer diameter, locating at a first location the first imperfection with respect to the length of the pipe and with respect to the outer diameter of the pipe. Such a method may include one or some of the following, in any possible combination: detecting a second part of the first imperfection in a second location adjacent the first location; detecting additional parts of the first imperfection in succeeding adjacent locations adjacent the first location and providing a presentation of data related to the first imperfection indicating an entire extent of the first imperfection and locations on the pipe of the extent; wherein the presentation is a map of the pipe's outer surface divided into a plurality of adjacent locations with data for each location representative of the detected parameter at each location; wherein the parameter of the pipe is wall thickness of the pipe; wherein the parameter of the pipe is representative of a flaw in the pipe; wherein the flaw in the pipe is from the group consisting of longitudinal flaw, transverse flaw and oblique flaw; wherein the parameter is pipe wall thickness and the first imperfection is detected by ultrasonic inspection apparatus; wherein pipe length is divided into a continuous series of length increments and the pipe outer diameter is divided into a continuous series of segments for each length increment, and the first location is a particular segment at a particular length increment; wherein the parameter is detected for increments along the entire length of the pipe and for segments around the entire circumference of the pipe for each said increments; wherein pipe length is divided into a continuous series of length increments and the pipe outer diameter is divided into a continuous series of segments for each length increment, and the first location is a particular segment at a particular length increment, and wherein a master computer instructs detecting apparatus to move from a first series of segments for a first linear increment that includes the first location to a next series of segments for a next linear increment only upon completion of detecting of the parameter for all segments of the first series of segments, and wherein the detecting is done by detecting apparatus that includes a plurality of spaced apart shoes, each with a plurality of spaced-apart ultrasonic transducers, the shoes rotatable around the pipe, the detecting apparatus including related ultrasonic transducer instrumentation for providing raw data representative of a detected parameter; detecting the parameter for all series of segments for all linear increments; and/or each segment having data representative of the parameter for that segment.

What is claimed is:

1. A method for inspecting pipe, the method comprising
   detecting at least a first part of a first imperfection in a parameter of a pipe, the pipe having a length, a hollow body, an outer surface, and a generally circular pipe wall with an inner diameter and an outer diameter,
   locating at a first location the first imperfection with respect to the length of the pipe and with respect to the outer diameter of the pipe,
   wherein pipe length is divided into a continuous series of length increments and the pipe outer diameter is divided into a continuous series of segments for each length increment, and the first location is a particular segment at a particular length increment, and wherein a master computer instructs detecting apparatus to move from a first series of segments for a first linear increment that includes the first location to a next series of segments for a next linear increment only upon completion of detecting of the parameter for all segments of the first series of segments, and wherein the detecting is done by detecting apparatus that includes a plurality of spaced apart shoes, each with a plurality of spaced-apart ultrasonic transducers, the shoes rotatable around the pipe, the detecting apparatus including related ultrasonic transducer instrumentation for providing raw data representative of a detected parameter.

2. The method of claim 1 further comprising
   detecting a second part of the first imperfection in a second location adjacent the first location.

3. The method of claim 1 further comprising
   detecting additional parts of the first imperfection in succeeding adjacent locations adjacent the first location and
   providing a presentation of date related to the first imperfection indicating en entire extent of the first imperfection and locations on the pipe of said extent.

4. The method of claim 3 wherein the presentation is a map of the pipe's outer surface divided into a plurality of adjacent locations with date for each location representative of the detected parameter at each location.

5. The method of claim 1 wherein the parameter of the pipe is wall thickness of the pipe.

6. The method of claim 1 wherein the parameter of the pipe is representative of a flaw in the pipe.

7. The method of claim 1 wherein the flaw in the pipe is from the group consisting of longitudinal flaw, transverse flaw and oblique flaw.

8. The method of claim 1 wherein the parameter is pipe wall thickness end the first imperfection is detected by ultrasonic inspection apparatus.

9. The method of claim 1 wherein pipe length is divided into a continuous series of length increments and the pipe outer diameter is divided into a continuous series of segments for each length increment, and the first location is a particular segment at a particular length increment.

10. The method of claim 1 wherein the parameter is detected for increments along the entire length of the pipe and for segments around the entire circumferences of the pipe for each said increments.

11. The method of claim 1 further comprising detecting the parameter for all series of segments for all linear increments.

12. The method at claim 1 further comprising each segment having data representative of the parameter for that segment.

13. A method for inspecting pipe, the method comprising moving detecting apparatus around a pipe.

moving the pipe through the detecting apparatus without rotating the pipe, detecting with the detecting apparatus as the detecting apparatus moves around the pipe an inspection parameter in at least a first part of the pipe the pipe having a length, a hollow body, an outer surface, and a generally circular pipe wall with an inner diameter and an outer diameter, locating ate first location the first part of the pipe with respect to the length of the pipe and with respect to the outer diameter of the pipe.

14. The method of claim 13 further comprising detecting the inspection parameter for a second part of the pipe in a second location adjacent the first location.

15. The method of claim 13 further comprising detecting the inspection parameter additional parts of the pipe in succeeding adjacent locations adjacent the first location and providing a presentation of data related to the inspection parameter for all inspected parts of the pipe and locations on the pipe of all of said parts.

16. The method of claim 15 wherein the presentation is a map of the pipe's outer surface divided into a plurality of adjacent locations with data for each location representative of the detect inspection parameter at each location.

17. The method of 13 wherein the inspection parameter of the pipe is wall thickness of the pipe.

18. The method of claim 13 wherein the inspection parameter of the pipe is representative of a flaw in the pipe.

19. The method of claim 13 wherein the inspection parameter is pipe wall thickness detected by ultrasonic inspection apparatus.

20. The method of claim 13 wherein pipe length is divided into a continuous series of length increments and the pipe outer diameter is divided into a continuous series of segments for each length increment, and the first location is a particular segment at a particular length increment.

21. The method of claim 13 wherein the detecting is done by detecting apparatus end the locating is done by a master computer to which is input location data representative of location of the detecting apparatus with respect to the pipe and to which master computer is input inspection parameter data from the detecting apparatus representative of the inspection parameter.

22. The method of claim 21 wherein the master computer correlates the location data with the inspection parameter data.

23. The method of claim 21 wherein the master computer adjusts location data to take into account an actual position of the detacting apparatus.

24. The method of claim 13 wherein the is length is divided into a continuous series of length increments and the pipe outer diameter is divided into a continuous series of segments for each length increment, and the first location is a particular segment at a particular length increment, and wherein the master computer instructs the detecting apparatus to move from a first series of segments for a first linear increment that includes the first location to a next series of segments for a next linear increment only upon completion of detecting of the inspection parameter for all segments of the first series of segments.

25. The method of claim 24 further comprising detecting the inspection parameter for all series of segments for all linear increments.

26. The method of claim 25 further comprising each segment having data representative of the inspection parameter for that segment.

27. A method for inspecting pipe, the method comprising moving inspecting apparatus around a pipe, moving the pipe through the detecting apparatus without rotating the pipe, detecting with the detecting apparatus as the detecting apparatus moves around the pipe at least a first part of a first imperfection in a parameter of the pipe, the pipe having a length, a hollow body, an outer surface, and a generally circular pipe wall with an inner diameter and an outer diameter, locating at a first location the first imperfection with respect to the length of the pipe and with respect to the outer diameter of the pipe.

28. The method of claim 27 further comprising detecting a second part of the first imperfection in a second location adjacent the first location.

29. The method of claim 27 comprising detecting additional parts of the first imperfection in succeeding adjacent locations adjacent the first location and providing a presentation of data related to the first imperfection indicating en entire extent of the first imperfection and locations on the pipe of said extent.

30. The method of claim 29 wherein the presentation is a map of the pipe's outer surface divided into a plurality of adjacent locations with data for each location representative of the detected parameter each location.

31. The method of claim 27 in the parameter of the pipe is wall thickness of the pipe.

32. The method of claim 27 wherein the parameter of the pipe is representative of a flaw in the pipe.

33. The method of claim 27 wherein the parameter is pipe wall thickness the first imperfection is detects ultrasonic inspection apparatus.

34. The method of claim 27 wherein pipe length is divided into a continuous series of length increments and the pipe outer diameter is divided into a continuous series of segments for each length increment, and the first locution is a particular segment at a particular length increment.

35. The method of claim 27 the parameter is detected for increments along the entire length of the pipe and for segments around the entire circumference of the pipe for each said increments.

* * * * *